(12) United States Patent
Kunzemann

(10) Patent No.: US 10,159,211 B2
(45) Date of Patent: Dec. 25, 2018

(54) DILL VARIETY 'TEDDY'

(71) Applicant: Enza Zaden Beheer B.V., Enkhuizen (NL)

(72) Inventor: Olaf Kunzemann, Dannstadt-Schauernheim (DE)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 15/715,868

(22) Filed: Sep. 26, 2017

(65) Prior Publication Data

US 2018/0092325 A1    Apr. 5, 2018

Related U.S. Application Data

(60) Provisional application No. 62/402,807, filed on Sep. 30, 2016.

(51) Int. Cl.
*A01H 5/12* (2018.01)
*A01H 6/06* (2018.01)

(52) U.S. Cl.
CPC .................. *A01H 5/12* (2013.01); *A01H 6/06* (2018.05)

(58) Field of Classification Search
None
See application file for complete search history.

(56) References Cited

PUBLICATIONS

UPOV Publication TG/165/3, Mar. 24, 1999.*

* cited by examiner

*Primary Examiner* — David H Kruse
(74) *Attorney, Agent, or Firm* — Morrison & Foerster LLP

(57) ABSTRACT

A new dill variety designated 'Teddy' is described. 'Teddy' is a dill variety exhibiting stability and uniformity.

15 Claims, 1 Drawing Sheet
(1 of 1 Drawing Sheet(s) Filed in Color)

DILL VARIETY 'TEDDY'

CROSS-REFERENCE TO RELATED APPLICATIONS

This application claims the benefit of U.S. Provisional Application No. 62/402,807, filed Sep. 30, 2016, which is hereby incorporated by reference in its entirety.

FIELD OF THE INVENTION

The present invention relates to the field of plant breeding. In particular, this invention relates to a new dill, *Anethum graveolens*, variety designated 'Teddy'.

BACKGROUND OF THE INVENTION

Dill, *Anethum graveolens*, is a popular annual herb having culinary uses. *Anethum graveolens* is in the Apiaceae (celery) family. Fresh and dried dill leaves are also known as dill weed to distinguish them from dill seed.

In cooking, dill is commonly used either fresh or dried to impart its distinctive flavor into various dishes. Dill seed is commonly used as a spice. Dill oil can be extracted from the leaves, stems and seeds of the plant. The oil from the seeds is distilled and used in the manufacturing of soaps Dill is an important and valuable herb. Accordingly, there is a need for new dill varieties. In particular, there is a need for improved dill varieties that are stable, high yielding, and agronomically sound.

SUMMARY OF THE INVENTION

In order to meet these needs, the present invention is directed to improved dill varieties.

As used herein dill variety 'Teddy' is the same dill variety as dill variety 'E10D7002' having NCIMB Accession Number X1 and disclosed in U.S. Provisional Application No. 62/402,807. While the name has changed, dill variety 'Teddy' has all the defining characteristics of dill variety 'E10D7002'.

In one embodiment, the present invention is directed to dill, *Anethum graveolens*, seed designated as 'Teddy' having NCIMB Accession Number 43074. In one embodiment, the present invention is directed to an *Anethum graveolens* dill plant and parts isolated therefrom produced by growing 'Teddy' dill seed. In another embodiment, the present invention is directed to an *Anethum graveolens* plant and parts isolated therefrom having all the physiological and morphological characteristics of a *Lactuca sativa* plant produced by growing 'Teddy' dill seed having NCIMB Accession Number 43074. In still another embodiment, the present invention is directed to an $F_1$ hybrid *Anethum graveolens* dill seed, plants grown from the seed, and a head isolated therefrom having 'Teddy' as a parent, where 'Teddy' is grown from 'Teddy' dill seed having NCIMB Accession Number 43074.

Dill plant parts include stems, leaves, parts of leaves, pollen, ovules, flowers, roots, cells, seeds, and the like. In another embodiment, the present invention is further directed to dill stems, leaves, parts of leaves, flowers, pollen, ovules, roots, seeds, or cells isolated from 'Teddy' dill plants. In another embodiment, the present invention is further directed to tissue culture of 'Teddy' dill plants, and to dill plants regenerated from the tissue culture, where the plant has all of the morphological and physiological characteristics of 'Teddy' dill plants.

In still another embodiment, the present invention is further directed to packaging material containing 'Teddy' plant parts. Such packaging material includes but is not limited to boxes, plastic bags, etc. The 'Teddy' plant parts may be combined with other plant parts of other plant varieties.

In yet another embodiment, the present invention is further directed to a method of selecting dill plants, by a) growing 'Teddy' dill plants where the 'Teddy' plants are grown from dill seed having NCIMB Accession Number 43074 and b) selecting a plant from step a). In another embodiment, the present invention is further directed to dill plants, plant parts and seeds produced by the dill plants where the dill plants are isolated by the selection method of the invention.

In another embodiment, the present invention is further directed to a method of breeding dill plants by crossing a dill plant with a plant grown from 'Teddy' dill seed having NCIMB Accession Number 43074. In still another embodiment, the present invention is further directed to dill plants, dill parts from the dill plants, and seeds produced therefrom where the dill plant is isolated by the breeding method of the invention.

In another embodiment, the present invention is directed to methods for producing a male sterile dill plant by introducing a nucleic acid molecule that confers male sterility into a dill plant produced by growing 'Teddy' dill seed, and to male sterile dill plants produced by such methods.

In another embodiment, the present invention is directed to methods of producing an herbicide resistant dill plant by introducing a gene conferring herbicide resistance into a dill plant produced by growing 'Teddy' dill seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant dill plants produced by such methods.

In another embodiment, the present invention is directed to methods of producing a pest or insect resistant dill plan by introducing a gene conferring pest or insect resistance into a dill plant produced by growing 'Teddy' dill seed, and to pest or insect resistant dill plants produced by such methods. In certain embodiments, the gene conferring pest or insect resistance encodes a *Bacillus thuringiensis* endotoxin.

In another embodiment, the present invention is directed to methods of producing a disease resistant dill plant by introducing a gene conferring disease resistance into a dill plant produced by growing 'Teddy' dill seed, and to disease resistant dill plants produced by such methods.

In another embodiment, the present invention is directed to methods of producing a dill plant with a value-added trait by introducing a gene conferring a value-added trait into a dill plant produced by growing 'Teddy' dill seed, where the gene encodes a protein selected from a ferritin, a nitrate reductase, and a monellin. Certain embodiments are also directed to dill plants having a value-added trait produced by such methods.

In another embodiment, the present invention is directed to methods of introducing a desired trait into dill variety 'Teddy', by: (a) crossing a 'Teddy' plant, where a sample of 'Teddy' dill seed was deposited under NCIMB Accession Number 43074, with a plant of another dill variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Teddy' plant to produce backcross progeny plants; (d) selecting for backcross progeny plants that have the desired trait and all of the physiological and morphological characteristics of dill variety 'Teddy'; and (e) repeating steps (c) and (d) two or more times in succession to produce selected third or higher backcross progeny plants that comprise the desired trait. Certain embodiments are also directed to dill plants produced by such methods, where the plants have the desired trait and all of the physiological and morphological characteristics of dill variety 'Teddy'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present invention provides for single gene converted plants of 'Teddy'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring dill gene or a transgene introduced through genetic engineering techniques.

In a further embodiment, the present invention relates to methods for developing dill plants in a dill plant breeding program using plant breeding techniques including recurrent selection, backcrossing, pedigree breeding, restriction fragment length polymorphism enhanced selection, genetic marker enhanced selection, and transformation. Seeds, dill plants, and parts thereof, produced by such breeding methods are also part of the invention.

In addition to the exemplary aspects and embodiments described above, further aspects and embodiments will become apparent by reference by study of the following description.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1A:
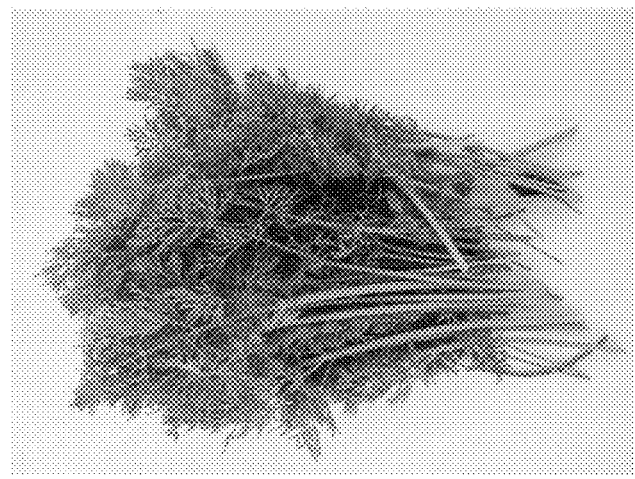
FIG. 1A shows leaves of dill variety 'Teddy'.

There are numerous steps in the development of novel, desirable dill germplasm. Plant breeding begins with the analysis of problems and weaknesses of current dill germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of dill plant breeding is to develop new, unique, and genetically superior dill varieties. A breeder can initially select and crosses two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial dill varieties thus requires the development of parental dill varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into dill varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable Umbelliferae," Rubatzky, V. E., et al. (1999).

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Bolting. The premature development of a flowering stalk, and subsequent seed, before a plant produces a food crop. Bolting is typically caused by late planting when temperatures are low enough to cause vernalization of the plants.

*Bremia lactucae*. An oomycete that causes downy mildew in leafy vegetables, such as lettuce and dill, in cooler growing regions.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Fusarium. Any of several fungi of the genus, *Fusarium*, which are causal agents of stem and root rot, such as *Fusarium* wilt. *Fusarium* wilt is characterized by damping-off, collapse of the plant, wilting, and a brown dry rot.

Gene. As used herein, "gene" refers to a segment of nucleic acid. A gene can be introduced into a genome of a species, whether from a different species or from the same species, using transformation or various breeding methods.

Maturity date. Maturity refers to the stage when the plants are of full size or optimum weight, in marketable form or shape to be of commercial or economic value.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Overview of the Variety 'Teddy'

Dill variety 'Teddy' is the result of numerous generations of plant selections chosen for its yield, short plant height, medium stem length and diameter, dense foliage, triangular leaf shape, dense leaf feathering, and medium time of beginning of flowering.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Teddy'.

Objective Description of the Variety 'Teddy'

Figure 1B:
FIG. 1B shows leaves of dill variety 'Green Sleeves'.
Figure 1C:
FIG. 1C shows leaves of dill variety 'Ella'.

Dill variety 'Teddy' has the following morphologic and other characteristics:

Young Plant:
Anthocyanin coloration: Absent
Attitude of leaves (3 to 5 leaves stage): Semi-erect
Plant:
Density of foliage: Dense
Number of primary branches: Medium
Height: Short
Stem:
Length of main stem: Medium
Diameter (at middle third): Medium
Blue hue: Absent
Intensity of green color: Medium
Waxiness: Medium
Leaves:
Shape: Triangular
Density of feathering: Dense
Width of segments: Medium
Length: Short
Width: Medium
Blue hue: Absent
Intensity of green color: Medium
Waxiness: Medium
Blade serration of margin: Present; similar to variety 'Purple Ruffles'
Blade depth of serration: Shallow; similar to 'Italian Large Leaf'
Blade undulation of margin: Absent or very weak; similar to variety 'Grand vert'
Main Umbel:
Diameter: Medium
Number of peduncles: Medium
Time of appearance of main umbel: Medium
Time of beginning of flowering: Medium Comparisons to Similar Varieties Table 1 below compares some of the characteristics of dill variety 'Teddy' with dill varieties 'Green Sleeves' and 'Ella'. Column 1 lists the characteristics, column 2 shows the characteristics for dill variety 'Green Sleeves', column 3 shows the characteristics for dill variety 'Ella', and column 4 shows the characteristics for dill variety 'Teddy'. Photographs of the dill varieties 'Teddy', 'Green Sleeves' and 'Ella' are depicted in FIG. 1A-1C.

TABLE 1

| Characteristic | 'Green Sleeves' | 'Ella' | 'Teddy' |
| --- | --- | --- | --- |
| Density of plant foliage | Medium | Medium-dense | Dense |
| Plant height | Tall | Medium | Short |
| Intensity of green color of leaf | Medium-dark | Dark | Medium |

Further Embodiments

Gene Conversions

When the term "dill plant" is used in the context of the present invention, this also includes any gene conversions of that variety. The term "gene converted plant" as used herein refers to those dill plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental dill plant which contributes the gene for the desired characteristic is termed the "nonrecurrent" or "donor parent." This terminology refers to the fact that the nonrecurrent parent is used one time in the backcross protocol and therefore does not recur. The parental dill plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a dill plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of dill and regeneration of plants therefrom is well known and widely published. For example, reference may be had to Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce dill plants having the physiological and morphological characteristics of variety 'Teddy'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a dill plant by crossing a first parent dill plant with a second parent dill plant where the first or second parent dill plant is a dill plant of variety 'Teddy'. Further, both first and second parent dill plants can come from dill variety 'Teddy'. Thus, any such methods using dill variety 'Teddy' are part of the invention: selfing, backcrosses, hybrid production, crosses to populations, and the like. All plants produced using dill variety 'Teddy' as at least one parent are within the scope of this invention, including those developed from varieties derived from dill variety 'Teddy'. Advantageously, this dill variety could be used in crosses with other, different, dill plants to produce the first generation ($F_1$) dill hybrid seeds and plants with superior characteristics. The variety of the invention can also be used for transformation where exogenous genes are introduced and expressed by the variety of the invention. Genetic variants created either through traditional breeding methods using dill variety 'Teddy' or through transformation of variety 'Teddy' by any of a number of protocols known to those of skill in the art are intended to be within the scope of this invention.

The following describes breeding methods that may be used with dill variety 'Teddy' in the development of further dill plants. One such embodiment is a method for developing variety 'Teddy' progeny dill plants in a dill plant breeding program, by: obtaining the dill plant, or a part thereof, of variety 'Teddy', utilizing said plant or plant part as a source of breeding material, and selecting a dill variety 'Teddy' progeny plant with molecular markers in common with variety 'Teddy' and/or with morphological and/or physiological characteristics selected from the characteristics listed in the section entitled "Objective description of the variety 'Teddy'." Breeding steps that may be used in the dill plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of dill variety 'Teddy' progeny dill plants, by crossing variety 'Teddy' with another dill plant, thereby producing a population of dill plants, which, on average, derive 50% of their alleles from dill variety 'Teddy'. A plant of this population may be selected and repeatedly selfed or sibbed with a dill variety resulting from these successive filial generations. One embodiment of this invention is the dill variety produced by this method and that has obtained at least 50% of its alleles from dill variety 'Teddy'. One of ordinary skill in the art of plant breeding would know how to evaluate the traits of two plant varieties to determine if there is no significant difference between the two traits expressed by those varieties. For example, see Fehr and Walt, *Principles of Variety Development,* pp. 261-286 (1987). Thus the invention includes dill variety 'Teddy' progeny dill plants containing a combination of at least two variety 'Teddy' traits selected from those listed in the section entitled "Objective description of the variety 'Teddy'," or the variety 'Teddy' combination of traits listed in the Summary of the Invention, so that said progeny dill plant is not significantly different for said traits than dill variety 'Teddy' as determined at the 5% significance level when grown in the same environmental conditions. Using techniques described herein, molecular markers may be used to identify said progeny plant as a dill variety 'Teddy' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of dill variety 'Teddy' may also be characterized through their filial relationship with dill variety 'Teddy', as for example, being within a certain number of breeding crosses of dill variety 'Teddy'. A breeding cross is a cross made to introduce new genetics into the progeny, and is distinguished from a cross, such as a self or a sib cross, made to select among existing genetic alleles. The lower the number of breeding crosses in the pedigree, the closer the relationship between dill variety 'Teddy' and its progeny. For example, progeny produced by the methods described herein may be within 1, 2, 3, 4, or 5 breeding crosses of dill variety 'Teddy'.

As used herein, the term "plant" includes plant cells, plant protoplasts, plant cell tissue cultures from which dill plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the dill variety 'Teddy' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of dill variety 'Teddy' were deposited on Jun. 12, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43074. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. Dill seed designated as 'Teddy', representative sample of seed having been deposited under NCIMB Accession Number 43074.

2. A dill plant produced by growing the seed of claim 1.

3. A plant part from the plant of claim 2.

4. The plant part of claim 3, wherein said part is a stem, a leaf, flower, or a portion thereof.

5. The plant part of claim 4, wherein said part is a leaf.

6. A dill plant having all the physiological and morphological characteristics of the dill plant of claim 2.

7. A plant part from the plant of claim 6.

8. The plant part of claim 7, wherein said part is a stem, a leaf, flower, or a portion thereof.

9. The plant part of claim 8, wherein said part is a leaf.

10. An $F_1$ hybrid dill plant having 'Teddy' as a parent where 'Teddy' is grown from the seed of claim 1.

11. A pollen grain or an ovule of the plant of claim 2.

12. A tissue culture of the plant of claim 2.

13. A dill plant regenerated from the tissue culture of claim 12, wherein the plant has all of the morphological and physiological characteristics of a dill plant produced by growing seed designated as 'Teddy', representative sample of seed having been deposited under NCIMB Accession Number 43074.

14. A method of making dill seeds, said method comprising crossing the plant of claim 2 with another dill plant and harvesting seed therefrom.

15. A method of making dill variety 'Teddy', said method comprising selecting seeds from the cross of one 'Teddy' plant with another 'Teddy' plant, a sample of 'Teddy' dill seed having been deposited under NCIMB Accession Number 43074.

* * * * *